United States Patent

Haga et al.

Patent Number: 5,463,052
Date of Patent: Oct. 31, 1995

[54] METHOD FOR PRODUCING BENZYLIDENE DERIVATIVES

[75] Inventors: Nobuhiro Haga; Masanao Inagaki, both of Osaka; Saichi Matsumoto, Ikeda; Susumu Kamata, Takarazuka, all of Japan

[73] Assignee: Shionogi & Co., Ltd., Osaka, Japan

[21] Appl. No.: 246,494

[22] Filed: May 20, 1994

[30] Foreign Application Priority Data

May 26, 1993 [JP] Japan .................................. 5-123909
Apr. 22, 1994 [JP] Japan .................................. 6-084438

[51] Int. Cl.⁶ ........................................... C07D 275/02
[52] U.S. Cl. ........................... 544/2; 544/63; 548/214
[58] Field of Search ........................ 548/214; 544/63, 544/2

[56] References Cited

U.S. PATENT DOCUMENTS

| | | | |
|---|---|---|---|
| 4,892,870 | 1/1990 | Lee | 514/211 |
| 5,093,363 | 3/1992 | Kita et al. | 514/532 |
| 5,246,952 | 9/1993 | Lans | 514/365 |

FOREIGN PATENT DOCUMENTS

| | | |
|---|---|---|
| 0414206 | 2/1991 | European Pat. Off. |
| 0525197 | 2/1993 | European Pat. Off. |
| 0595546 | 5/1994 | European Pat. Off. |
| 2634764 | 2/1990 | France |

OTHER PUBLICATIONS

J. Sung et al., Drugs of the Future, "BF–389", 17 (1): 12–14 (1992).

S. Wong et al., Agents Actions, "Antiarthritic Profile of BF–389—A Novel Anti–Inflammatory Agent With Low Ulcerogenic Liability", 37: 90–98 (1992).

C. Orlando, Jr., J. Org. Chem., "Quinone Methide Chemistry. The Benzylic Oxidative Methoxylation of 2,6–Di–tert–butyl–p–cresol", vol. 35, No. 11, 3714–3717 (1970).

Primary Examiner—Robert Gerstl
Attorney, Agent, or Firm—Wenderoth, Lind & Ponack

[57] ABSTRACT

A selective and high-yield method is described for producing stereoisomeric benzylidene derivatives of the formula III:

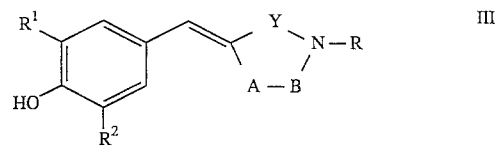

wherein $R^1$ and $R^2$ each independently is lower alkyl, lower alkoxy or halogen; Y is $SO_2$, SO or CO; —A— is optionally substituted lower alkylene; —B— is —$CH_2$— or —O—; or —A— and —B— taken together may form optionally substituted phenylene or optionally substituted lower alkenylene; and R is hydrogen, optionally substituted lower alkyl, cycloalkyl, lower alkoxy, hydroxy, optionally substituted aryl, optionally substituted arylalkyl; optionally substituted arylalkyloxy, heterocyclic ring or N-protecting groups, which comprises reacting a compound of the formula I:

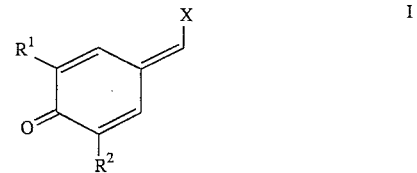

wherein $R^1$ and $R^2$ are as defined above and X is lower alkoxy or halogen with a compound of the formula II:

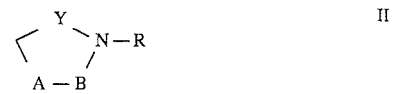

wherein Y, —A—, —B— and R are as defined above in the presence of a base.

5 Claims, No Drawings

METHOD FOR PRODUCING BENZYLIDENE DERIVATIVES

FIELD OF THE INVENTION

This invention relates to novel method for producing benzylidene derivatives which have an ability to a suppress the production of $PGE_2$, $LTB_4$ and IL-1, and can be useful as excellent non-steroidal anti-inflammatory agents.

BACKGROUND OF THE INVENTION

Benzylidene derivatives represented by the following general formula III

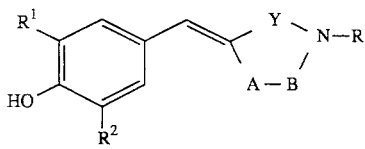

wherein $R^1$ and $R^2$ each independently is lower alkyl, lower alkoxy or halogen; Y is $SO_2$, SO or CO; —A— is optionally substituted lower alkylene; —B— is —$CH_2$— or —O—; or —A— and —B— taken together may form optionally substituted phenylene or optionally substituted lower alkenylene; and R is hydrogen, optionally substituted lower alkyl, cycloalkyl, lower alkoxy, hydroxy, optionally substituted aryl, optionally substituted arylalkyl; optionally substituted arylalkyloxy, heterocyclic ring or N-protecting group are known to include many pharmaceutically useful compounds. For example, it has been suggested that a compound of the formula III wherein —A— is —$CH_2CH_2$—, —B— is —O—, Y is CO, R is —$CH_3$, and $R^1$ and $R^2$ are both t-butyl can be useful as an anti-inflammatory agent with low ulcerogenic potential. Sung J. L. et al., Drugs of the Future 17(1): 12–14 (1992); and S. Wong et al., Agents Actions 37: 90–98 (1992). It has also been found that a kind of benzylidene derivatives of the formula III have an ability to suppress the production of $PGE_2$, $LTB_4$ and IL-1 in vitro and prevent edema with little damages of gastric mucosa in vivo, and can be excellent non-steroidal anti-inflammatory agents. These are disclosed in EP Appln. No. 93308369.3 (Publication No. 595546) corresponding to U.S. patent application Ser. No. 08/142,146.

These benzylidene derivatives of the formula III can be prepared in a conventional manner, for example, according to the following reaction scheme.

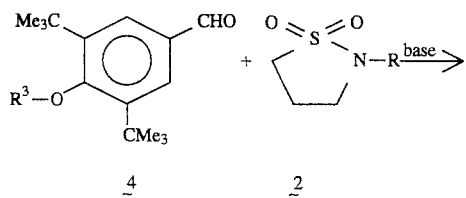

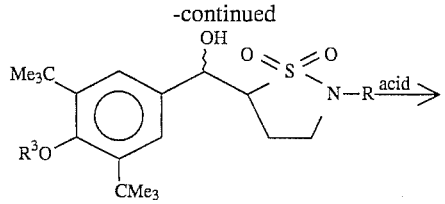

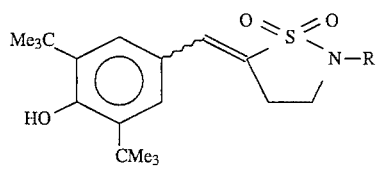

In the reaction scheme above, R is a as defined above and $R^3$ is hydroxy-protecting group in EP patent application No. 93308369.3 (Publication No. 595546) corresponding to U.S. patent application No. 08/142,146. Thus, hydroxy-protected 3,5-di-tert-butyl-4-hydroxybenzaldehyde 4 is reacted with γ-sultam derivative 2 under a conditions for aldol reaction to obtain an aldol addition compound 5. The compound 1, when deprotected and dehydrated in the presence of an acid, gives the objective benzylidene derivative 3' as a mixture of stereoisomers in (E)- and (Z) forms, which is then subjected to resolution, when a given isomer is desired. For example, a compound of the formula 3' wherein R is —$CH_3$ (5-(3,5-di-tert-butyl-4-hydroxybenzylidene)-2-methyl-1,2-isothiazolidine-1,1-dioxide), when tested to evaluate inhibitory activity against the production of $PGE_2$ in rat synovial membrane cells, against the production of $LTB_4$ in rat celiac cells, or against the production of IL-1 under LPS stimulation in THP-1 cells, showed different activities as follows.

|     | $PGE_2$ (Rat SVC) | $LTB_4$ (Rat PEC) | L-1 (THP-1) $IC_{50}$ (μM) |
|-----|-------------------|-------------------|----------------------------|
| (E) | <0.001            | 2.8               | 21                         |
| (Z) | <0.001            | 1.8               | 29                         |

The separation of isomers of compounds shown by the formula III, however, is difficult and requires troublesome procedures, which prevented the industrial production of objective benzylidene derivatives. Therefore, a novel method for producing compounds III, especially an isomer thereof, which is stereoselective and applicable to industrial process, is needed to promote the development of medicinal drugs such as non-steroidal anti-inflammatory agents.

DESCRIPTION OF THE INVENTION

The present inventors have made intensive researches with purpose to establish a method for producing selectively a desired isomer of a compound of the formula III and found that an objective stereoisomer of high purity can be prepared in high yield by reacting a quinone methide compound and a nitrogen-containing heterocyclic compound in the presence of a base.

Thus, the present invention provides a method for producing benzylidene derivatives of the formula III, which comprises reacting a compound of the formula I:

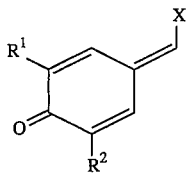

wherein $R^1$ and $R^2$ each independently is lower alkyl, lower alkoxy or halogen; and X is lower alkoxy or halogen with a compound of the formula II:

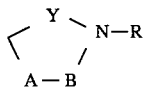

wherein Y is $SO_2$, SO or CO; —A— is optionally substituted lower alkylene; —B— is —$CH_2$— or —O—; or —A— and —B— taken together may form optionally substituted phenylene or optionally substituted lower alkenylene; and R is hydrogen, optionally substituted lower alkyl!, cycloalkyl, lower alkoxy, hydroxy, optionally substituted aryl, optionally substituted arylalkyl; optionally substituted arylalkyloxy, heterocyclic ring or N-protecting group in the presence of a base.

According to the method of the present invention, a desired pharmaceutically active benzylidene derivative of the formula III can be obtained in stereoselective manner by treating a quinone methide compound of the formula I (i.e., 4-methylene-2,5-cyclohexadienone derivative) substituted with a leaving group X with an anion prepared by treating a heterocyclic compound of the formula II with a base such as an organolithium compound.

For purposes of the present invention, as disclosed and claimed herein, the following terms are defined below.

The term "lower alkyl" means straight or branched chain $C_1$–$C_8$ alkyl, for example, methyl, ethyl, n-propyl, i-propyl, n-butyl, i-butyl, s-butyl, t-butyl, n-pentyl, i-pentyl, neopentyl, s-pentyl, t-pentyl, n-hexyl, neohexyl, i-hexyl, s-hexyl, t-hexyl, heptyl and octyl. Preferable lower alkyl group is a straight or branched chain $C_1$–$C_4$ alkyl and the most preferable one is methyl or ethyl.

The term "lower alkoxy" means straight or branched chain alkoxy of 1 to 6 carbon atoms, for example, methoxy, ethoxy, n-propoxy, i-propoxy, n-butoxy, i-butoxy, s-butoxy, t-butoxy, n-pentyloxy, i-pentyloxy, neopentyloxy, s-pentyloxy, t-pentyloxy, n-hexyloxy, neohexyloxy, i-hexyloxy, s-hexyloxy and t-hexyloxy. Preferably lower alkoxy group is a $C_1$–$C_3$ alkoxy and most preferably it is methoxy.

The term "halogen" means fluorine, chlorine, bromine and iodine and preferably one is chlorine.

The term "lower alkylene" means a group formed by taking a hydrogen atom from each carbon at both ends of a linear alkane of $C_1$–$C_5$, preferably, $C_1$–$C_4$. Examples of lower alkylene include methylene, ethylene and propylene.

The term "lower alkenylene" means a group formed by taking a hydrogen atom from each carbon at both ends of a linear alkene of $C_2$–$C_5$, preferably, $C_2$–$C_4$. Examples of lower alkenylene include vinylene, propenylene, butenylene and the like.

Examples of substituents in the definition of "optionally substituted phenylene" include halogen, lower alkyl, lower alkoxy and the like.

Examples of substituents in the definition of "optionally substituted alkylene" include lower alkyl, hydroxyalkyl, alkoxyalkyl, lower alkoxy, hydroxy, phenyl and the like. Phenyl may have a substituent(s).

Examples of substituents in the definition of "optionally substituted alkenylene" include lower alkyl, hydroxyalkyl, alkoxyalkyl, lower alkoxy, phenyl and the like. Phenyl may have a substituent(s).

The term "heterocyclic ring" means a cyclic group containing 1–4 hetero atoms selected from sulfur, nitrogen and oxygen, for example, pyridyl, furfuryl, thienyl, thiazolyl, isothiazolyl, oxazolyl, isoxazolyl, imidazolyl, triazolyl and tetrazolyl.

The term "cycloalkyl" means cycloalkyl of 3–7 carbon atoms, for example, cyclopropyl, cyclobutyl, cyclopentyl, cyclohexyl and cycloheptyl. A $C_3$–$C_5$ cycloalkyl, particularly cyclopropyl, is preferred.

The term "aryl" means phenyl or naphthyl. As defined by the term "optionally substituted aryl", aryl may have one or more substituents selected from halogen, lower alkoxy, lower alkyl, nitro and trifluoromethyl. Examples of optionally substituted aryl include phenyl, 4-chlorophenyl, 4-methoxyphenyl, 4-methylphenyl, 4-nitrophenyl, 3,4-dichlorophenyl, 3,4-dimethoxyphenyl, 3,4-dinitrophenyl, 1-naphthyl and 2-naphthyl.

The term "arylalkyl" means a group formed by substituting a lower alkyl group as defined above with an aryl group(s), which may be substituted with one or more substituent(s) similar to those described in the definition for "optionally substituted aryl". Examples of optionally substituted arylalkyl include benzyl, 4-chlorobenzyl, 4-methoxybenzyl, 4-methylbenzyloxy, 3,4-dichlorobenzyl, 3,4-dimethoxybenzyl, 4-nitrobenzyl, 2-phenylethyl, 2-(4-chlorophenyl)ethyl, 2-(4-methoxyphenyl)ethyl, 1-naphthylmethyl and 2-naphthylmethyl with a preference in benzyl.

The term "arylalkyloxy" means a group formed by substituting a lower alkoxy group as defined above with an aryl group(s), which may be substituted with one or more substituent(s) similar to those described in the definition for "optionally substituted aryl". Examples of optionally substituted arylalkyloxy include benzyloxy, 4-chlorobenzyloxy, 4-methoxybenzyloxy, 4-methylbenzyloxy, 3,4-dichlorobenzyloxy, 3,4-dimethoxybenzyloxy, 4-nitrobenzyloxy, 2-phenylethyloxy, 2-(4-chlorophenyl)ethyloxy, 2-(4-methoxyphenyl)ethyloxy, 1-naphthylmethyloxy and 2-naphthylmethyloxy with a preference in benzyloxy.

Examples of substituents in the definition of "substituted lower alkyl" include halogen, hydroxy, lower alkoxy, amino, lower alkylamino, di-lower-alkylamino and the like.

N-protecting groups usable in the present method can be selected from those conventionally used in the art, for example, tert-butoxycarbonyl, benzyloxycarbonyl, benzyl, 4-methoxybenzyl, 3,4-dimethoxybenzyl, 4-nitrobenzyl, trimethylsilyl, dimethyl-tert-butylsilyl, diphenyl-tert-butylsilyl and the like.

Bases usable in the present invention are organolithium compounds such as n-butyllithium, sec-butyllithium, tert-butyllithium, phenyllithium, lithium diisopropylamide (LDA), lithium bis(trimethylsilyl)amide (LiHMDS) and the like. LDA and LiHMDS are preferred.

The present methods can be effected by using any starting compounds I and II though, there are certain preferable compounds, for example, compounds I wherein X is lower alkoxy, especially methoxy, and compounds II wherein Y is $SO_2$. The most preferred compound to be produced is (E)-5-(3,5-di-tert-butyl-4-hydroxybenzylidene)-2-ethyl-1,2-isothiazolidine-1,1-dioxide.

The method of the present invention will be explained below in detail employing certain compounds to facilitate understanding. These compounds are used simply for illustrative purpose, and one of ordinary skill in the art can easily anticipate that any compounds of the formula III can be prepared according to the present invention by selecting appropriate starting materials.

Step 1

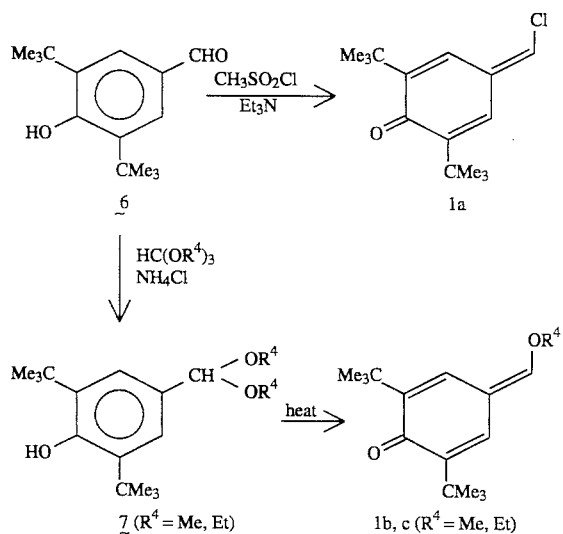

The starting material, quinone methide 1 (i.e., 4-substituted methylene-2,6-di-tert-butyl-2,5-cyclohexadiene-1-one) (compound I) can be prepared by any one of known methods in the art. Thus, compounds of the formula I wherein X is halogen and those wherein X is lower alkoxy can be prepared according to teachings in U.S. Pat. No. 5,093,363 corresponding to EP Publication No. 414206 and J. Org. Chem. 35, 3714–3717 (1970), respectively, as shown in the reaction scheme above.

Compound 1a (4-chloromethylene-2,6-di-tert-butyl-2,5-cyclohexadiene-1-one) can be obtained by treating 3,5-Di-tert-butyl-4-hydroxybenzaldehyde 6 with methane sulfonyl chloride in the presence of triethylamine.

Compounds 1b and [b ]1[; ]c wherein $R^4$ is methyl and ethyl, respectively are readily obtained by converting compound 6 into acetal compound 7 in a conventional manner and heating the resultant compound 7.

Step 2: Reaction of Compounds I and II

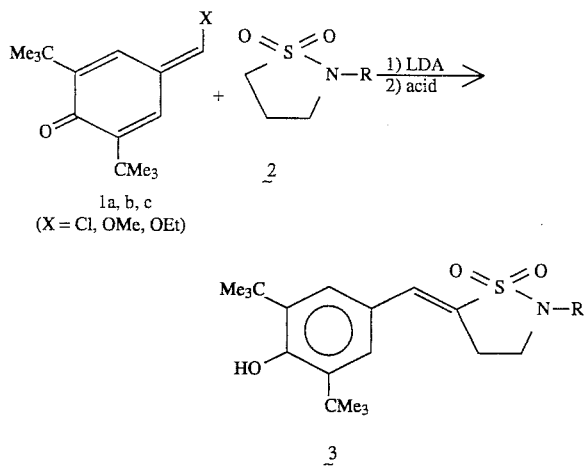

Prior to the reaction, compound (2) is treated with a base, especially with an organolithium compound, to generate an anion. Examples of organolithium compounds usable in the present method include those commonly used in the field of organic chemistry such as n-butyllithium, sec-butyllithium, tert-butyllithium, phenyllithium, lithium diisopropylamide (LDA), lithium bis(trimethylsilyl)amide (LiHMDS) and the like. Reaction is carried out in a solvent selected from ether solvents such as ether, tetrahydrofuran (THF), dimethoxyethane, dioxane and the like; and hydrocarbon solvents such as n-hexane, benzene, toluene and the like, or a mixture thereof, in the presence of hexamethylphosphoramide (HMPA), tetramethylethylenediamine and the like, preferably in a single solvent of THF.

About 0.1 to 2 equivalents, preferably 0.5 to 1 equivalent of a quinone methide prepared in step 1 (e.g., compound 1a–c) is reacted with an anion of compound 2 prepared above at about −100° to 50° C., preferably at −70° to 0° C. until the reaction is complete. The resultant product is treated with an appropriate acid to give the desired compound 3. Examples of acids usable include inorganic acids such as hydrochloride and organic acids such as p-toluenesulfonic acid.

The following Examples are provided to further illustrate the present invention and are not to be construed as limiting thereof.

Preparation 1

Preparation of 4-Chloromethylene-2,6-di-tert-butyl-2,5-cyclohexadiene-1-one (1a)

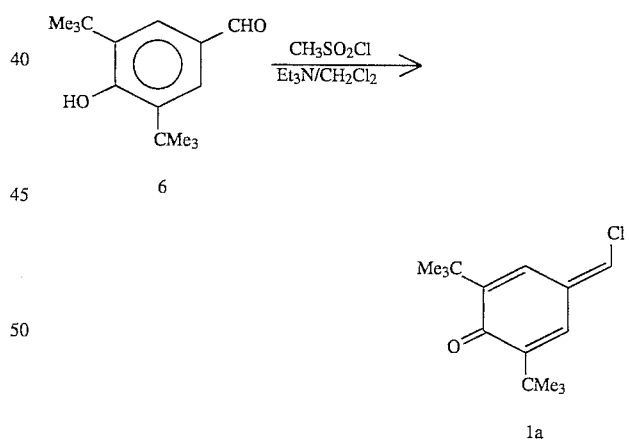

To a solution of 3,5-di-tert-butyl-4-hydroxybenzaldehyde (6) (7.02 g, 30 mmole) in methylene chloride (70 ml) was added dropwise triethylamine (8.36 ml, 60 mmole). After the addition of methanesulfonyl chloride (4.7 ml, 60 mmole), the mixture was heated to reflux for 5 hr. The resultant reaction mixture was concentrated under reduced pressure to yield the crude product (1a) (8.156 g), which was used in the next step without further purification.

NMR(CDCl$_3$) δ ppm: 1.28(9H, s), 1.32(9H, s), 6.81(1H, d, J=2.4 Hz), 7.42(1H, d, J=2.4 Hz).

Preparation 2

Preparation of 2,6-di-tert-Butyl-4-methoxymethylene-2,5-cyclohexadiene-1-one (1b)

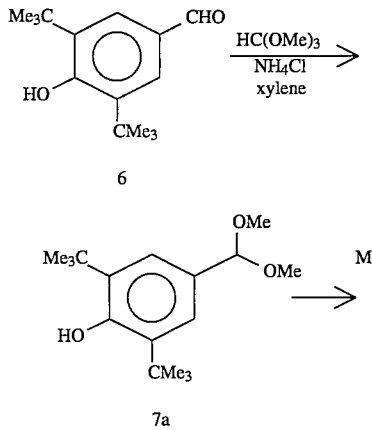

To anhydrous xylene (60 ml) were added compound (6) (23.4 g, 0.1 mole), ethyl orthoformate (60 ml) and absolute methanol (60 ml) successively. After addition of ammonium chloride (2 g), the mixture was heated to reflux for 1 hr. The resultant reaction mixture was concentrated at ordinary pressure to distill off about 150 ml of solvent. The residue was cooled to room temperature by adding anhydrous xylene (200 ml) and filtered through a cotton plug to remove ammonium chloride. The filtrate was heated to reflux for 24 hr in Dean-Stark apparatus equipped with 4A molecular sieves and concentrated under reduced pressure to yield a brown crystalline residue. The residue, when recrystallized from a mixture of petroleum ether and ligroin, gave the objective compound (1b) (20.32 g, 82%). M.p. 137°–139° C.

NMR ($D_6$-acetone) δ ppm: 1.61(9H, s), 1.64(9H, s), 4.43(3H, s), 3.68(1H, d, J=2.2 Hz), 7.76–7.82(2H, m).

Preparation 3

Preparation of 2,6-di-tert-Butyl-4-ethoxymethylene-2,5-cyclohexadiene-1-one (1c)

Compound (6) (23.4 g, 0.1 mole), ethyl orthoformate (60 ml), absolute methanol (60 ml) and ammonium chloride (2 g) were reacted in anhydrous xylene (60 ml) and the resultant reaction mixture was treated in a manner similar to that described in Preparation 2 to yield the objective compound (1c) (22.01 g, 84%). M.p. 114°–117° C.

NMR ($D_6$-acetone) δ ppm: 1.61(9H, s), 1.64(9H, s), 1.75(3H, t, J=7.0 Hz), 4.69(2H, q, J=7.0 Hz), 3.68(1H, d, J=2.2 Hz), 7.76–7.82(2H, m).

EXAMPLE 1

Preparation of (E)-5-(3,5-di-tert-Butyl-4-hydroxybenzylidene)-2-ethyl-1,2-isothiazolidine-1,1-dioxide (3a) by Method (A)

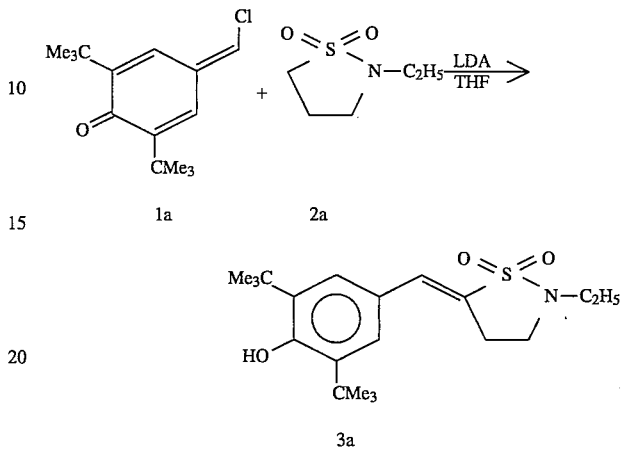

Lithium diisopropylamide (hereinafter, referred to as LDA) solution was prepared by adding dropwise diisopropylamine (10.58 ml, 73 mmole) to a solution of n-butyllithium in n-hexane (1.68M, 39 ml, 66 mmole) with stirring and ice-cooling over 20 min followed by stirring for another 15 min. The LDA solution was cooled to −78° C. and combined with THF (60 ml) and hexamethylphosphoramide (hereinafter, referred to as HMPA) (12 ml). To the resultant solution was added dropwise a solution of N-ethyl-1,2-isothiazolidine-1,1-dioxide (2a) (4.47 g, 30 mmole) in THF (30 ml) at −70° to −65° C., and the mixture stirred at −70° C. for 30 min. To the reaction mixture was added dropwise a solution of crude 4-chloromethylene-2,6-di-tert-butyl-2,5-cyclohexadien-1-one (1a) (30 mmole) prepared in Preparation 1 above in THF (30 ml) at −70° to −65° C. After stirring at −70° C. for 30 min and then at room temperature for 1 hr, the reaction mixture was poured into ice-cooled water containing 2N HCl (40 ml) and extracted with ethyl acetate (350 ml) (×2). The ethyl acetate solution was washed with water (50 ml) (×3) and a saturated brine (50 ml), dried over anhydrous sodium sulfate, and distilled under reduced pressure to remove the solvent. The residue (12.73 g) was dissolved in toluene (150 ml). To the solution was added p-toluenesulfonic acid (p-TsOH) hydrate (1.87 g, 9.8 mmole) and the mixture heated to reflux for 30 min. The reaction mixture was poured into dilute aqueous solution of sodium hydrogencarbonate (100 ml) and extracted with ethyl acetate (300 ml). The organic layer was washed with water (150 ml) followed by a saturated brine (150 ml), dried over anhydrous sodium sulfate and distilled under reduced pressure to remove the solvent. The residue, when purified by the use of column chromatography on silica gel eluting with toluene/ethyl acetate (2:1) and recrystallized from dichloromethane/diisopropyl ether, gave 1.86 g (17%) of the objective compound (3a). M.p. 135°–137° C.

NMR ($CDCl_3$) δ ppm: 1.29(3H, t, J=7.2 Hz), 1.45(18H, s), 3.07–3.19(4H, m), 3.28(2H, q, J=7.2 Hz), 5.50(1H, s), 7.24–7.26(3H, m).

Elementary analysis ($C_{20}H_{31}NO_3S$) Calcd.: C, 65.71; H, 8.55; N, 3.83; S, 8.77 Found: C, 65.65; H, 8.43; N, 3.85; S, 8.78.

Example 2

Preparation of Compound (3a) by Methods (B) and (C)

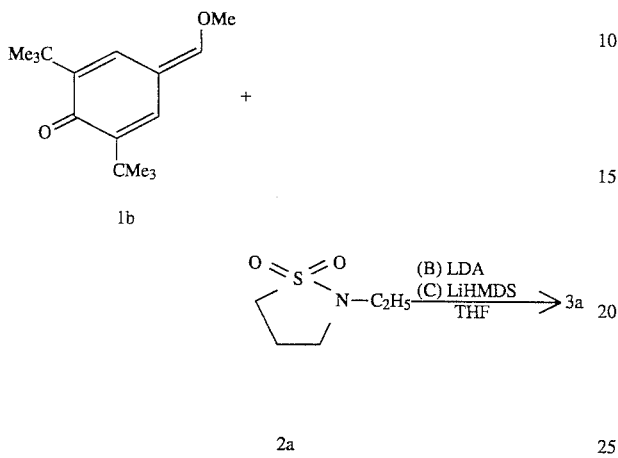

2a (1) Method (B)

LDA solution was prepared by adding dropwise diisopropylamine (29.72 ml, 0.21 mole) to a solution of n-butyllithium in n-hexane (1.60M, 125 ml, 0.2 mole) with stirring and ice-cooling over 20 min followed by stirring for another 15 min. The LDA solution was cooled to −78° C. and combined with THF (320 ml). To the resultant solution was added dropwise a solution of N-ethyl-1,2-isothiazolidine-1,1-dioxide (2a) (29.84 g, 0.2 mole) in THF (60 ml) at −70° to −65° C. After stirring at −70° C. for 30 min, to the reaction mixture was added dropwise a solution of 2,6-di-tert-butyl-4-methoxymethylene-2,5-cyclohexadiene-1-one (1b) (24.8 g, 0.1 mole) prepared in Preparation 2 above in THF (60 ml) at −70° to −65° C. The reaction mixture was warmed to −30° C. and stirred for 2.5 hr, poured into ice-cooled water containing 2N HCl (226 ml) and extracted with ethyl acetate (500 ml) (×2). The organic layer was washed with water (200 ml) and a saturated brine (200 ml), dried over anhydrous sodium sulfate, and distilled under reduced pressure to remove the solvent. The residue (48.77 g), when recrystallized from dichloromethane/diisopropyl ether, gave 30.2 g (83%) of the objective compound (3a).

(2) Method (C)

Procedures herein employed were substantially the same as those described in Method (B) above except that lithium bis(trimethylsilyl)amide (LiHMDS) was used instead of LDA.

To a solution of compound (2a) (7.625 g, 51.1 mmole) in THF (50 ml) was added dropwise a solution of LiHMDS (1.0M in THF) (56.2 ml, 56.2 mmole) with stirring and ice-cooling and the resultant mixture stirred at room temperature for 30 min. To the reaction mixture was added dropwise a solution of compound (1b) (6.35 g, 25.5 mmole) prepared in Preparation 2 above in THF (60 ml) with stirring and cooling at −55° to −48° C. The reaction mixture was gradually warmed to room temperature over about 1 hr. After the reaction is complete, the reaction product was treated in a similar manner as that described in (1) above to yield the objective compound (3a) (5.0 g, 54%).

EXAMPLE 3

Preparation of Compound (3a) by Method (D)

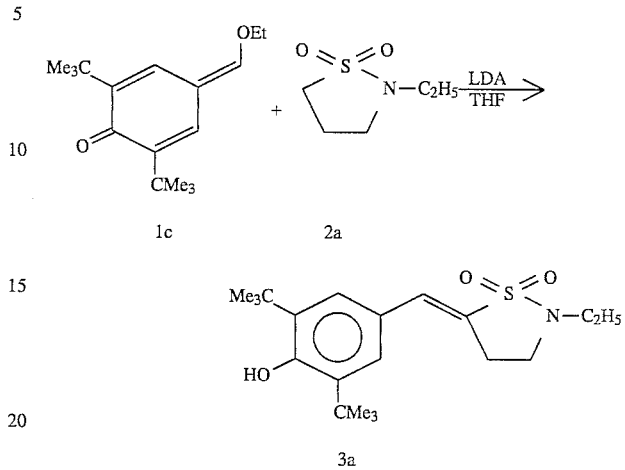

LDA solution was prepared by adding dropwise diisopropylamine (7.43 ml, 52.5 mole) to a solution of n-butyllithium in n-hexane (1.60M, 31 ml, 50 mmole) with stirring and ice-cooling over 20 min followed by stirring for another 15 min. The LDA solution was cooled to −78° C. and combined with THF (80 ml). To the resultant solution was added dropwise a solution of compound (2a) (7.46 g, 50 mmole) in THF (15 ml) at −70° to −65° C. and stirred at −70° C. for 30 min. To the reaction mixture was added dropwise a solution of 2,6-di-tert-butyl-4-ethoxymethylene-2,5-cyclohexadiene-1-one (1c) (6.56 g, 25 mmole) prepared in Preparation 3 in THF (15 ml) at −70° to −65° C. The reaction mixture was warmed to −30° C., stirred for 4.0 hr, poured into ice-cooled water containing 1N HCl (130 ml), and extracted with ethyl acetate (300 ml) (×2). The organic layer was washed with water (100 ml) and a saturated brine (200 ml), dried over anhydrous sodium sulfate, and distilled under reduced pressure to remove the solvent.

The residue (13.8 g), when recrystallized from dichloromethane/diisopropyl ether, gave 6.01 g (66%) of the objective compound (3a).

EXAMPLE 4

Preparation of (E)-5-(3,5-di-tert-Butyl-4-hydroxybenzylidene)-2-methyl-1,2-isothiazolidine-1,1-dioxide (3b)

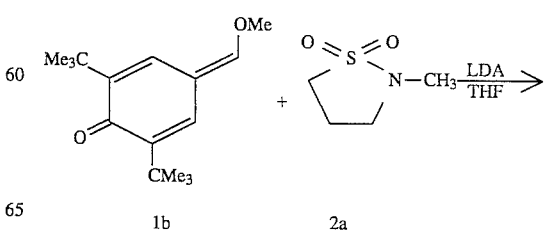

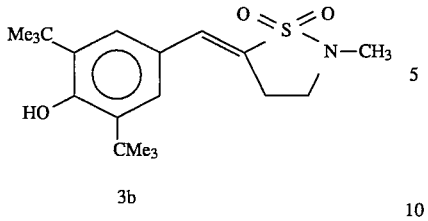

3b

LDA solution was prepared by adding dropwise diisopropylamine (9.34 ml, 72 mmole) to a solution of n-butyllithium in N-hexane (1.60M, 39 ml, 66 mmole) with stirring and ice-cooling over 20 min followed by stirring for another 15 min. The LDA solution was cooled to −78° C. and combined with THF (160 ml). To the resultant solution was added dropwise a solution of N-methyl-1,2-isothiazolidine-1,1-dioxide (2b) (8.96 g, 60 mmole) in THF (40 ml) at −70° to −65° C. and the mixture stirred at −70° C. for 30 min. To the reaction mixture was added dropwise a solution of compound (1b) (7.45 g, 30 mmole) prepared in Preparation 2 above in THF (40 ml) at −70° to −65° C. After stirring at −70° C. for 1 hr, the reaction mixture was poured into ice-cooled water containing 1N HCl (170 ml) and extracted with ethyl acetate (300 ml) (×2). The organic layer was washed with water (200 ml) and a saturated brine (200 ml), dried over anhydrous sodium sulfate, and distilled under reduced pressure to remove the solvent. The residue (17.8 g) was dissolved in toluene (350 ml). To the solution was added p-toluenesulfonic acid (p-TsOH) hydrate (3.70 g, 19.5 mmole) and the mixture heated to reflux for 30 min at 125° C. The reaction mixture was poured into saturated aqueous solution of sodium hydrogen-carbonate (150 ml) and extracted with ethyl acetate (150 ml). The organic layer was washed with saturated aqueous solution of sodium bicarbonate (150 ml), water (100 ml) and a saturated brine (100 ml), dried over anhydrous sodium sulfate and distilled under reduced pressure to remove the solvent. The residue, when recrystallized from dichloromethane/diisopropyl ether to give 7.31 g (69%) of the objective compound (3b). M.p. 168°–170° C.

NMR (CDCl$_3$) δ ppm: 1.45(18H, s), 2.76(3H, s), 3.07–3.18(2H, m), 3.20–3.32(2H, m), 5.51(1H, s), 7.23–7.29(3H, m).

Elementary analysis (C$_{19}$H$_{29}$NO$_3$S) Calcd.: C, 65.71; H, 8.55; N, 3.83; S, 8.77 Found : C, 65.65; H, 8.43; N, 3.85; S, 8.78.

EXAMPLE 5

Preparation of 2-Cyclopropyl-5-(3,5 -di-tert-Butyl-4-hydroxybenzylidene)-1,2-isothiazolidine-1,1-dioxide (3c)

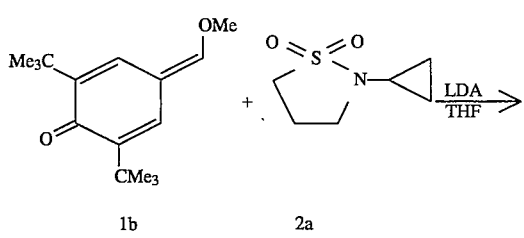

1b  2a

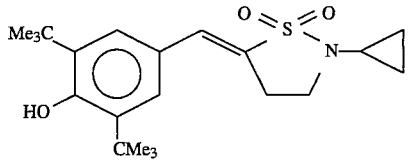

3c

In accordance with the method described in Example 2 (1) above, the objective compound (3c) was obtained by preparing LDA solution from a solution of n-butyllithium in n-hexane (1.60M, 12.5 ml, 20 mmole) and diisopropylamine (2.97 ml, 21 mmole), adding THF (20 ml) to the LDA solution, reacting the resultant mixture with a solution of N-cyclopropyl-1,2-isothiazolidine-1,1-dioxide (2c) (3.22 g, 20 mmole) in THF (10 ml) and then with a solution of compound (1b) (2.48 g, 10 mmole) in THF (10 ml), and treating the resultant reaction mixture in the same manner as described above. Yield, 2.57 g (68%); m.p. 202°–204° C.

NMR (CDCl$_3$) δ ppm: 0.68–0.90(4H, m), 1.44(18H, s), 2.28–2.40(1H, m), 3.08(2H, dt, J=2.6, 6.7 Hz), 3.36(2H, t, J=6.7 Hz), 5.51(1H, s), 7.20–7.25(3H, m).

Elementary analysis (C$_{21}$H$_{31}$NO$_3$S) Calcd.: C, 66.81; H, 8.28; N, 3.71; S, 8.49 Found: C, 66.76; H, 8.03; N, 3.72; S, 8.41.

EXAMPLE 6

Preparation of 5-(3,5-di-tert-Butyl-4-hydroxybenzylidene)-2-methoxy-1,2-isothiazolidine-1,1-dioxide (3d)

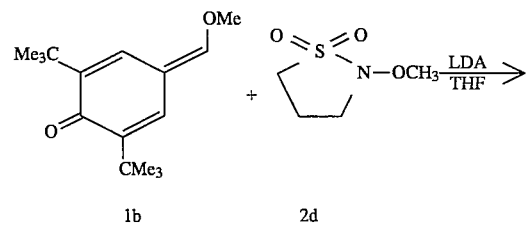

1b  2d

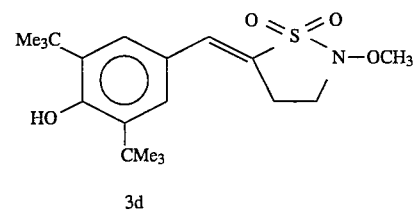

3d

In accordance with the method described in Example 2 (1) above, the objective compound (3d) was obtained by preparing LDA solution from a solution of n-butyllithium in n-hexane (1.60M, 12.5 ml, 20 mmole) and diisopropylamine (2.97 ml, 21 mmole), adding THF (20 ml) to the LDA solution, reacting the resultant mixture with a solution of N-methoxy-1,2-isothiazolidine-1,1-dioxide (2d) (2.48 g, 20 mmole) in THF (10 ml) and then with a solution of compound (1b) (2.48 g, 10 mmole) in THF (10 ml), and treating the resultant reaction mixture in the same manner as described above. Yield, 2.46 g (67%); m.p. 166°–168° C.

NMR (CDCl$_3$) δ ppm: 1.45(18H, s), 3.11(2H, dt, J=2.8, 7.0 Hz), 3.66(2H, t, J=7 Hz), 3.81(3H, s), 5.55(1H, s), 7.25–7.35(3H, m).

Elementary analysis (C$_{19}$H$_{29}$NO$_4$S) Calcd.: C, 62.10; H, 7.95; N, 3.81; S, 8.72 Found: C, 61.90; H, 7.88; N, 3.91; S, 8.67.

EXAMPLE 7

Preparation of (E)-5-(3,5-di-tert-Butyl-4-hydroxybenzylidene)-2-phenyl-1,2-isothiazolidine-1,1,-dioxide (3e)

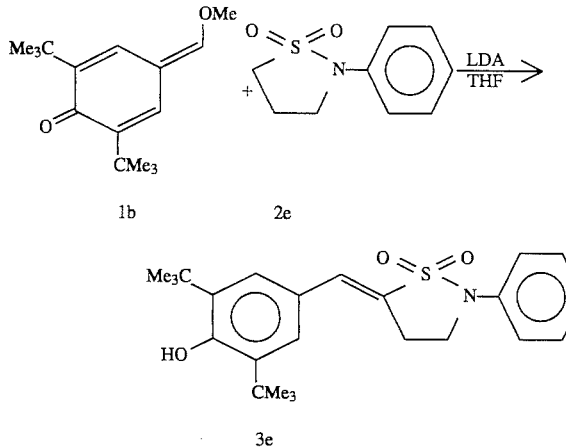

In accordance with the method described in Example 2 (1) above, the objective compound (3e) was obtained by preparing LDA solution from a solution of n-butyllithium in n-hexane (1.60M, 12.5 ml, 20 mmole) and diisopropylamine (2.97 ml, 21 mmole), adding THF (20 ml) to the LDA solution, reacting the resultant mixture with a solution of N-phenyl-1,2-isothiazolidine-1,1-dioxide (2e) (3.95 g, 20 mmole) in THF (10 ml) and then with a solution of compound (1b) (2.48 g, 10 mmole) in THF (10 ml), and treating the resultant reaction mixture in the same manner as described above. Yield, 2.27 g (55%); m.p. 195°–196° C.

NMR (CDCl$_3$) δ ppm: 1.47(18H, s), 3.31(2H, d, t, J=2.6, 6.6 Hz), 3.80(2H, t, J=6.6 Hz), 5.54(1H, s), 7.17–7.26(3H, m).

Elementary analysis (C$_{24}$H$_{31}$NO$_3$S) Calcd.: C, 69.70; H, 7.56; N, 3.39; S, 7.75 Found: C, 69.68; H, 7.47; N, 3.32; S, 7.71.

EXAMPLE 8

Preparation of (E)-4-(3,5-di-tert-Butyl-4-hydroxybenzylidene)-2-methyl-3,4,5,6 -tetrahydro-1,2-oxazin-3-one (3f)

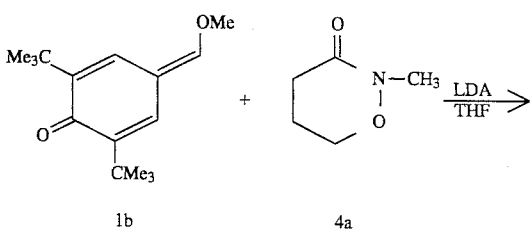

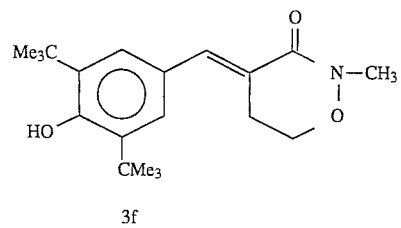

In accordance with the method described in Example 2 (1) above, a solution of LDA in THF (710 ml) was prepared from a solution of n-butyllithium in n-hexane (1.63M, 174 ml, 283.6 mmole) and diisopropylamine (37.8 ml, 283.5 mmole), to which were added dropwise a solution of compound (1b) (31.1 g, 270 mmole) in THF (200 ml) and compound (4a) (26.8 g, 108 mmole) in THF (300 ml) successively with stirring and cooling at –50° to –55° C., and the resultant reaction mixture was gradually warmed up to room temperature over about 1.5 hr. The reaction mixture was treated with a saturated aqueous solution of ammonium chloride (1.2 l) and extracted with ethyl acetate (1.2 l). The ethyl acetate extract was washed with water (1 l), dried over anhydrous sodium sulfate and distilled under reduced pressure to remove the solvent. The residue was chromatographed on silica gel. The objective compound (3f), which is a known compound in Drugs of the Future 17 (1): 12–14 (1992), was obtained from fractions eluted with n-hexane/ ethyl acetate (5:1). Yield, 15.19 g (42%); m.p., 174°–176° C.

IR (KBR) cm$^{-1}$: 3223, 1642, 1574, 1437, 1194.

NMR (CDCl$_3$) δ ppm: 1.45(18H, s, 2×$^t$Bu), 3.04(2H, dt, J=2.2, 6.0 Hz, CH2), 3.35(3H, s, CH3), 4.20(2H, t, J=6.0 Hz, CH2), 5.45(1H, s, OH), 7.32(2H, s, 2×-ArH), 7.76(1H, t, J=2.2 Hz, CH).

Elementary analysis (C$_{20}$H$_{29}$NO$_3$) Calcd.: C, 72.47; H, 8.82; N, 4.23 Found: C, 72.43; H, 8.86; N, 4.29.

EXAMPLE 9

Preparation of (E)-6-(3,5-di-tert-Butyl-4-hydroxybenzylidene)-2-methyl-4,5-dihydro-6H-1,3,2 -thiaoxazin-1,1-dioxide (3g)

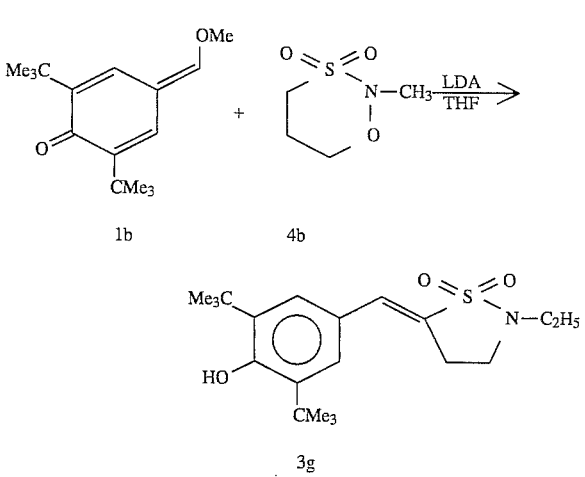

In accordance with the method described in Example 2 (1) above, to a solution of LDA prepared from a solution of n-butyllithium in n-hexane (1.60M, 2.5 ml, 20 mmole) and diisopropylamine (2.97 ml, 21 mmole) was added THF (20 ml) and the resultant solution was reacted with a solution of compound (4b) (3.03 g, 20 mmole) in THF (10 ml) and compound (1b) (2.48 g, 10 mmole) in THF (10 ml) successively. The resultant reaction mixture was treated in a similar manner as above to yield the objective compound (3g). Yield, 2.31 g (63%); m.p., 215°–216.5° C.

NMR (CDCl₃) δ ppm: 1.44(18H, s, 2×Buᵗ), 3.00(3H, s, CH3), 3.26–3.32(2H, m, CH2), 4.12–4.17(2H, m, CH2), 5.49(1H, s, OH), 7.15(2H, s, Ar—H), 7.55(1H, broad, CH).

Elementary analysis (C₁₉H₂₉NO₄S) Calcd.: C, 62.10; H, 7.95; N, 3.81; S, 8.72 Found: C, 62.03; H, 7.91; N, 3.92; S, 8.51.

EXAMPLE 10

Preparation of (E)-5-(3,4-di-tert-Butyl-4-hydroxybenzylidene)-2-(4-methoxybenzyl)-1,2-isothiazolidine-1,1-dioxide (3h)

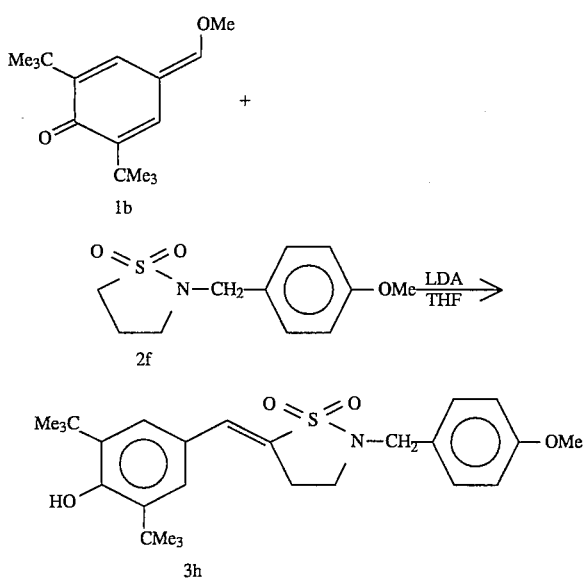

In accordance with the method described in Example 2 (1) above, to a solution of LDA prepared from a solution of n-butyllithium in n-hexane (1.60M, 81 ml, 0.130 mole) and diisopropylamine (18.5 ml, 0.132 mole) was added THF (80 ml) and the resultant solution was reacted with a solution of compound (2f) (28.98 g, 0.120 mole) in THF (120 ml) and compound (1b) (15 g, 60 mmole) in THF (120 ml) successively. The resultant reaction mixture was treated in a similar manner as above to yield the objective compound (3h). Yield, 25.55 g (93%); m.p., 189°–192° C.

NMR (CDCl₃) δ ppm: 1.44(18H s, 2× Buᵗ), 3.03–3.18(4H, m, 2×CH₂), 3.81(3H, s, OMe), 4.16(2H, s, CH2), 5.50(1H, s, OH), 6.88(2H, d, J=8.8 Hz, 2×Ar—H), 7.24–7.27(5H, m, 4×Ar—H+CH).

Elementary analysis (C₂₆H₃₅NO₄S) Calcd.: C, 68.24; H, 7.71; N, 3.06; S, 7.01 Found: C, 68.08; H, 7.70; N, 3.08; S, 6.96.

As is described above, the present invention provides a method for effective and stereoselective preparation of benzylidene derivatives of the formula III including pharmaceutically useful compounds such as non-steroidal anti-inflammatory agents in high yield, and thereby rendering industrial production thereof available and contributing to the improvement of researche and development of medicinal drugs.

What is claimed is:

1. A method for producing compounds of the formula III:

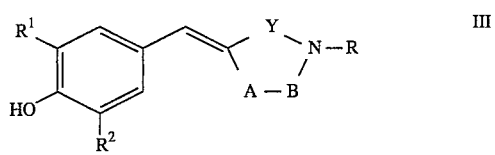

wherein $R^1$ and $R^2$ each independently is lower alkyl, lower alkoxy or halogen; Y is $SO_2$, SO or CO; —A— is optionally substituted lower alkylene; —B— is —$CH_2$— or —O—; or —A— and —B— taken together may form optionally substituted phenylene or optionally substituted lower alkenylene; and R is hydrogen, optionally substituted lower alkyl, cycloalkyl, lower alkoxy, hydroxy, optionally substituted aryl, optionally substituted arylalkyl; optionally substituted arylalkyloxy, heterocyclic ring or N-protecting group, which comprises reacting a compound of the formula I:

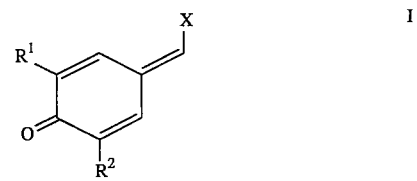

wherein $R^1$ and $R^2$ are as defined above and X is lower alkoxy with a compound of the formula II:

wherein Y, —A—, —B— and R are as defined above in the presence of a base.

2. The method as claimed in claim 1, wherein X is methoxy.

3. The method as claimed in claim 1, wherein Y is $SO_2$.

4. The method as claimed in claim 1, wherein the base is an organolithium compound.

5. The method as claimed in claim 4, wherein the base is lithium diisopropylamide or lithium bis(trimethylsilyl)amide.

* * * * *

UNITED STATES PATENT AND TRADEMARK OFFICE
CERTIFICATE OF CORRECTION

PATENT NO. :
DATED       :   5,463,052
INVENTOR(S) :   October 31, 1995
                Nobuhiro HAGA et al.

It is certified that error appears in the above-indentified patent and that said Letters Patent is hereby corrected as shown below:

Column 14, lines 55-60:

Formula 3g shown as " 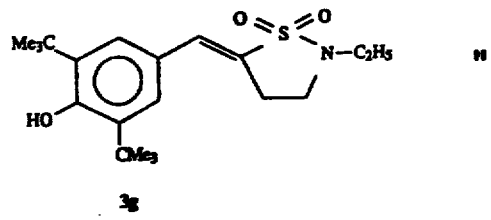 "

should read -- 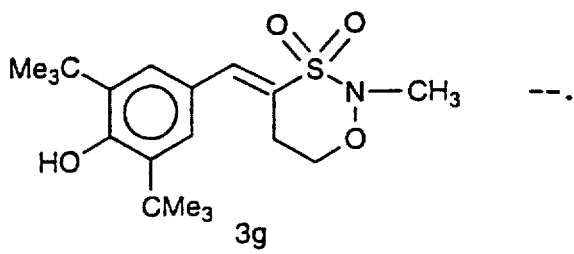 --.

Signed and Sealed this

Twenty-seventh Day of February, 1996

Attest:

BRUCE LEHMAN

Attesting Officer            Commissioner of Patents and Trademarks